United States Patent [19]

Meilland

[11] Patent Number: Plant 6,405

[45] Date of Patent: Nov. 22, 1988

[54] ROSE PLANT—MEIVROFIX VARIETY

[75] Inventor: Marie-Louise Meilland, Antibes, France

[73] Assignee: The Conard-Pyle Company, West Grove, Pa.

[21] Appl. No.: 895,489

[22] Filed: Aug. 11, 1986

[51] Int. Cl.[4] ..... A01H 5/00

[52] U.S. Cl. ..... Plt./18

[58] Field of Search ..... Plt. 18–20

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which forms attractive pink blossoms which are lightly bicolor on the under surface. The blossoms generally are borne one per stem and exhibit long lasting qualities when cut. The new variety forces well and particularly is suited for the production of cut flowers under greenhouse conditions.

2 Drawing Sheets

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was an unintroduced variety produced by a pair of crosses. Initially the product of the cross of the Meichim variety and the Meiban variety was crossed with the Jack Frost variety (U.S. Plant Pat. No. 2,522) to produce the female parent. The male parent (i.e., the pollen parent) of the new variety was formed by crossing the Meidirapo variety with an unintroduced seedling. The parentage of the new variety can be summarized as follows:

[(Meichim × Meiban) × Jack Frost] × (Meidirapo × unintroduced seedling).

The seeds resulting from the above pollination were sown and 28 plantlets were obtained which were physically and biologically different from each other. Selective study resulted in the identification of a single plant of the new variety.

The new variety meets well the needs of the floricultural industry for all uses and is particularly suited for the production of cut flowers.

It was found that the new variety of Hybrid Tea rose plant of the present invention possesses the following combination of characteristics:

(a) forms in abundance attractive long lasting very double pink blossoms which generally are borne one per stem,
(b) exhibits an excellent capacity for forcing, and
(c) is particularly well suited for growing under greenhouse conditions for the production of cut flowers.

The new variety has been found to undergo asexual propagation. The characteristics of the new variety have been found to be strictly transmissible by such asexual propagation from one generation to another.

The new variety has been named the Meivrofix variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were observed during January while grafted on *Rosa indica* understock and growing in a greenhouse at Cap d'Antibes, France. The true bud and blossom colorations are more accurately depicted in FIG. 17 than in the other illustrations.

DETAILED DESCRIPTION

Figures 1, 2, 3, 4, 5, 6, 7, 8, 9, 10, 11, 12, 13, 14, 15, 16:
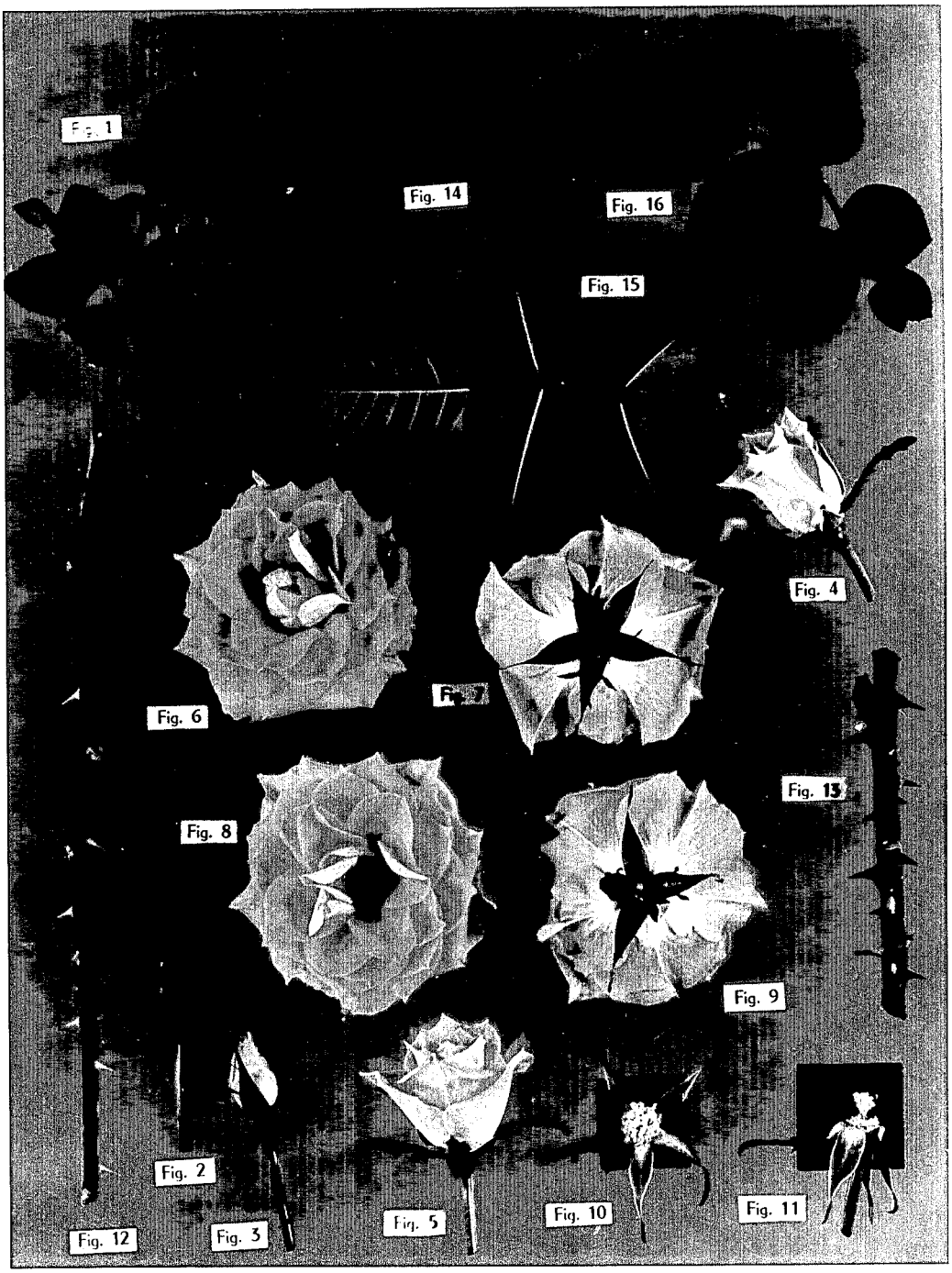
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a speciman of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—upper surface.
FIG. 15 illustrates a specimen of leaf with five leaflets—under surface.
FIG. 16 illustrates a specimen of a leaf with seven leaflets—upper surface.
Figure 17:
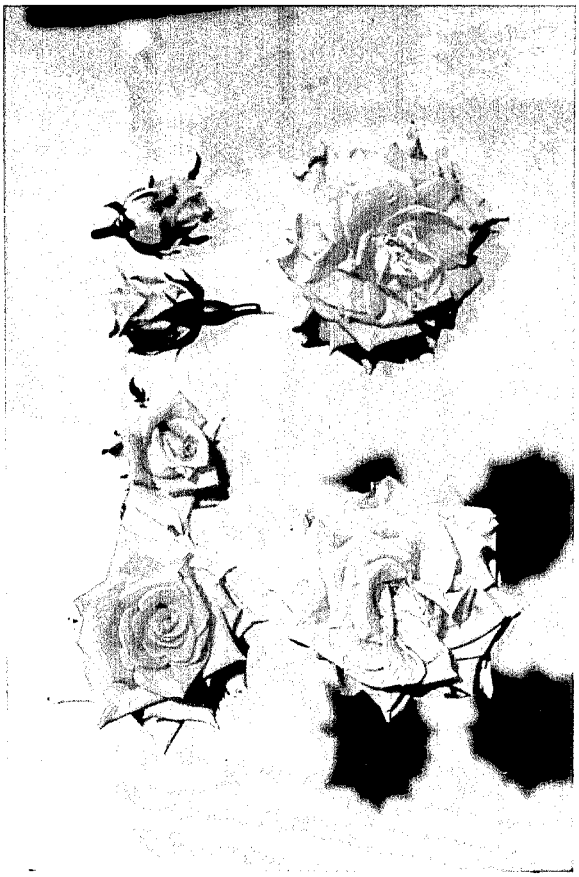
FIG. 17 illustrates buds and flowers in various stages of opening in which the coloration is more accurately depicted.

The chart used in the identification of the colors is that of The Royal Horticultural Society (R.H.S. Colour Chart). The description is based on specimens of the new variety during January while grafted on *Rosa indica* understock and growing in a greenhouse at Cap d'Antibes, France.

Class: Hybrid Tea.

Plant:

*Height.*—Plants which were pruned to a height of 85 cm. produced floral stems having an average length of approximately 30 to 50 cm.

*Habit.*—Upright, erect.

Branches:

*Color.*—Young stems: Yellow-Green Group 144A, more or less spotted with reddish brown coloration. Adult wood: medium green, Yellow-Green Group 147B.

Leaves:

*Petioles.*—Upper surface: grooved, reddish brown on young foliage and medium green on adult foliage. Under surface: light green, some small hooked thorns are present.

*Leaflets.*—Number: 3, 5, and 7 (most often). Shape: elliptic to ovate, round base, acute apex; the first leaves formed often exhibit malformation. Serrations: simple and regular. Color (young foliage): upper surface: bronze green, Yellow-Green Group 146A, largely suffused with reddish brown. under surface: bronze green, Yellow-Green Group 146A, largely suffused with reddish brown. Color (adult foliage): upper surface: Green Group 136A. under surface: Light green, Green Group 137C.

Inflorescence:

*Number of flowers.*—Generally one per stem.

*Peduncle.*—Medium green, straight, rigid, lightly glandular, approximately 5 to 6 cm. in length on average.

*Buds.*—Shape: oblong. Length: approximately 2.5 cm. on average. Color upon opening: upper surface: Red-Purple Group 57B. under surface: Whitish, largely suffused in Bengal Pink, Red-Purple Group 57C.

*Flower.*—Diameter: approximately 10 cm. on average. Color (when opening begins): upper surface: Pink, Red-Purple Group 57C. under surface: Whitish, largely suffused with pink, Red-Purple Group 57C. Color (when partially open): upper surface: pink, Red-Purple Group 57C. under surface: pink, Red-Purple Group 57C, more or less mottled with white. Fragrance: slight. Lasting quality: long. Petal number: approximately 30 on average. Petal form: rounded with a point at the tip and edges which are reflected. Stamen number: approximately 97 on average. Anthers: normal, yellow bordered with ochre coloration. Pistils: approximately 59 on average.

I claim:

1. A new and distinct variety of Hybrid Tea rose plant characterized by the following combination of characteristics:

(a) forms in abundance attractive long lasting very double pink blossoms which generally are borne one per stem, (b) exhibits an excellent capacity for forcing, and (c) is particularly well suited for growing under greenhouse conditions for the production of cut flowers;

substantially as herein shown and described together with the parts thereof.

* * * * *